US00PP35195P3

(12) United States Plant Patent
Olesen

(10) Patent No.: US PP35,195 P3
(45) Date of Patent: May 30, 2023

(54) ***ROSA HYBRIDA* PLANT NAMED 'POULREN043'**

(50) Latin Name: *Rosa hybrida*
Varietal Denomination: Poulren043

(71) Applicant: Mogens Nyegaard Olesen, Fredensborg (DK)

(72) Inventor: Mogens Nyegaard Olesen, Fredensborg (DK)

(73) Assignee: Poulsen Roser Als, Fredensborg (DK)

( * ) Notice: Subject to any disclaimer, the term of this patent is extended or adjusted under 35 U.S.C. 154(b) by 0 days.

(21) Appl. No.: 17/803,617

(22) Filed: Sep. 13, 2022

(65) Prior Publication Data

US 2023/0103294 P1 Mar. 30, 2023

(30) Foreign Application Priority Data

Sep. 24, 2021 (QZ) ..... PBR 2021/2350

(51) Int. Cl.
*A01H 5/02* (2018.01)
*A01H 6/74* (2018.01)

(52) U.S. Cl.
USPC ..... Plt./137
CPC ..... *A01H 6/749* (2018.05)

(58) Field of Classification Search
USPC ..... Plt./137
CPC ..... A01H 6/749; A01H 5/02
See application file for complete search history.

(56) References Cited

PUBLICATIONS

Poulsen Roser A/S (retrieved from Google Search on Nov. 10, 2022).*
CPVO Register (retrieved from CPVO Search on Nov. 10, 2022).*

* cited by examiner

*Primary Examiner* — Keith O. Robinson

(57) ABSTRACT

A new garden rose plant of the Hybrid Tea class which has abundant, pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulren043'.

This application claims priority to Plant Breeder's Rights Application Number 2021/2350, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren043', originated as a single seedling from the stated cross.

The new variety may be distinguished from its male pollen parent and female seed parent primarily by the following characteristics. The male pollen parent plant grows to a height of 80 to 90 cm, while the new variety grows to a height of 45 to 50 cm. The female seed parent plant has flowers with about 45 flower petals while the new variety has about 100 flower petals.

The objective of the hybridization of this rose variety was to create a new and distinct variety with unique qualities, such as:

1. Uniform and abundant pink flowers with strong perfume;
2. Vigorous, but compact growth when propagated on its own roots;
3. Exceptional disease resistance.

This combination of qualities is not present in previously available commercial cultivars of this type, known to the inventor, and distinguish 'Poulren043' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren043' was selected in the spring of 2014 by the inventor as a single plant from the progeny of the aforementioned hybridization.

Asexual reproduction of 'Poulren043' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren043' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren043'.

Specifically illustrated in FIG. 1 of the drawings are open flowers viewed from above and the side, flower petals detached revealing reproductive flower parts, detached sepals revealing the shape and colour of the receptacle and pedicel.

Figure 1:
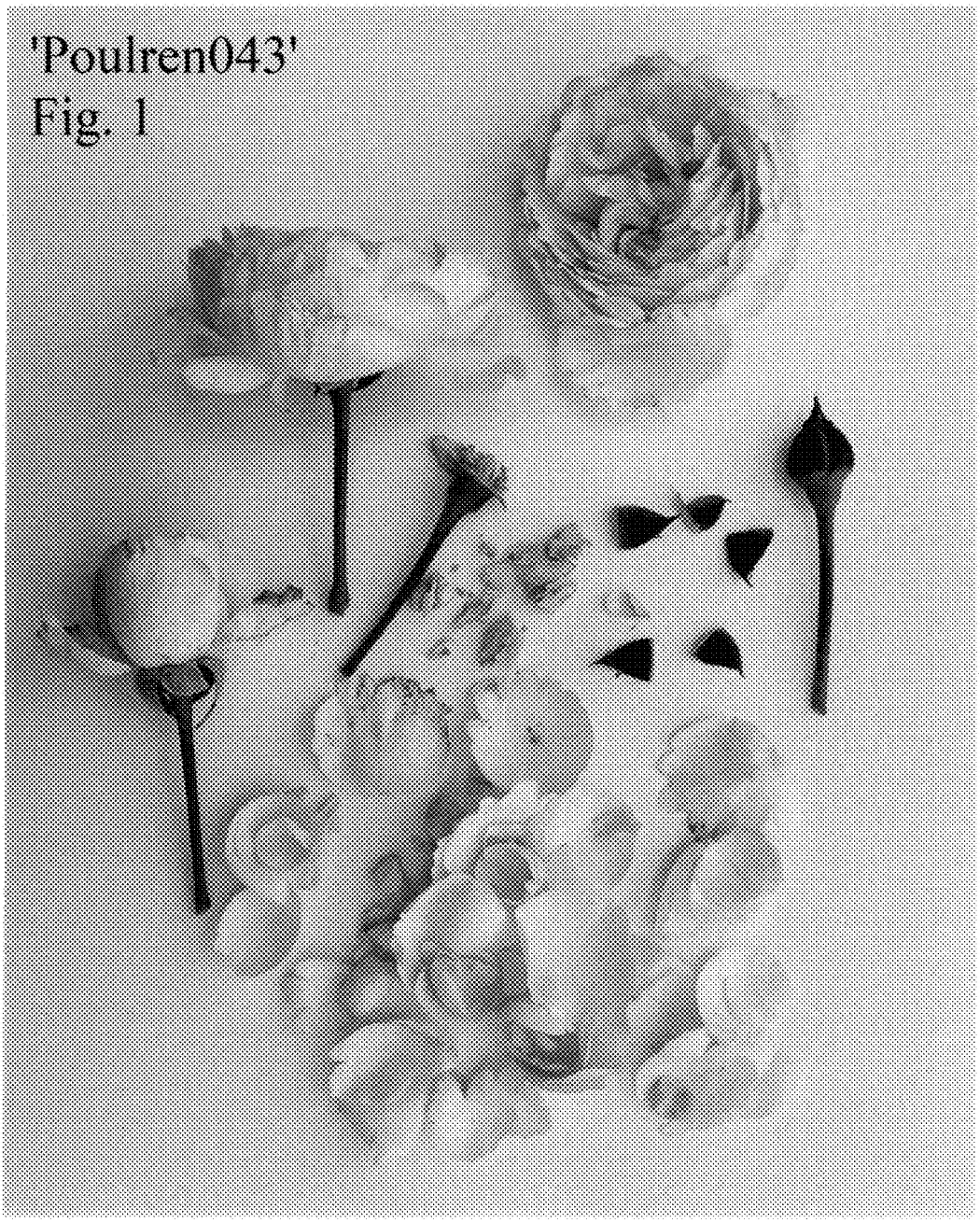
Figure 2:
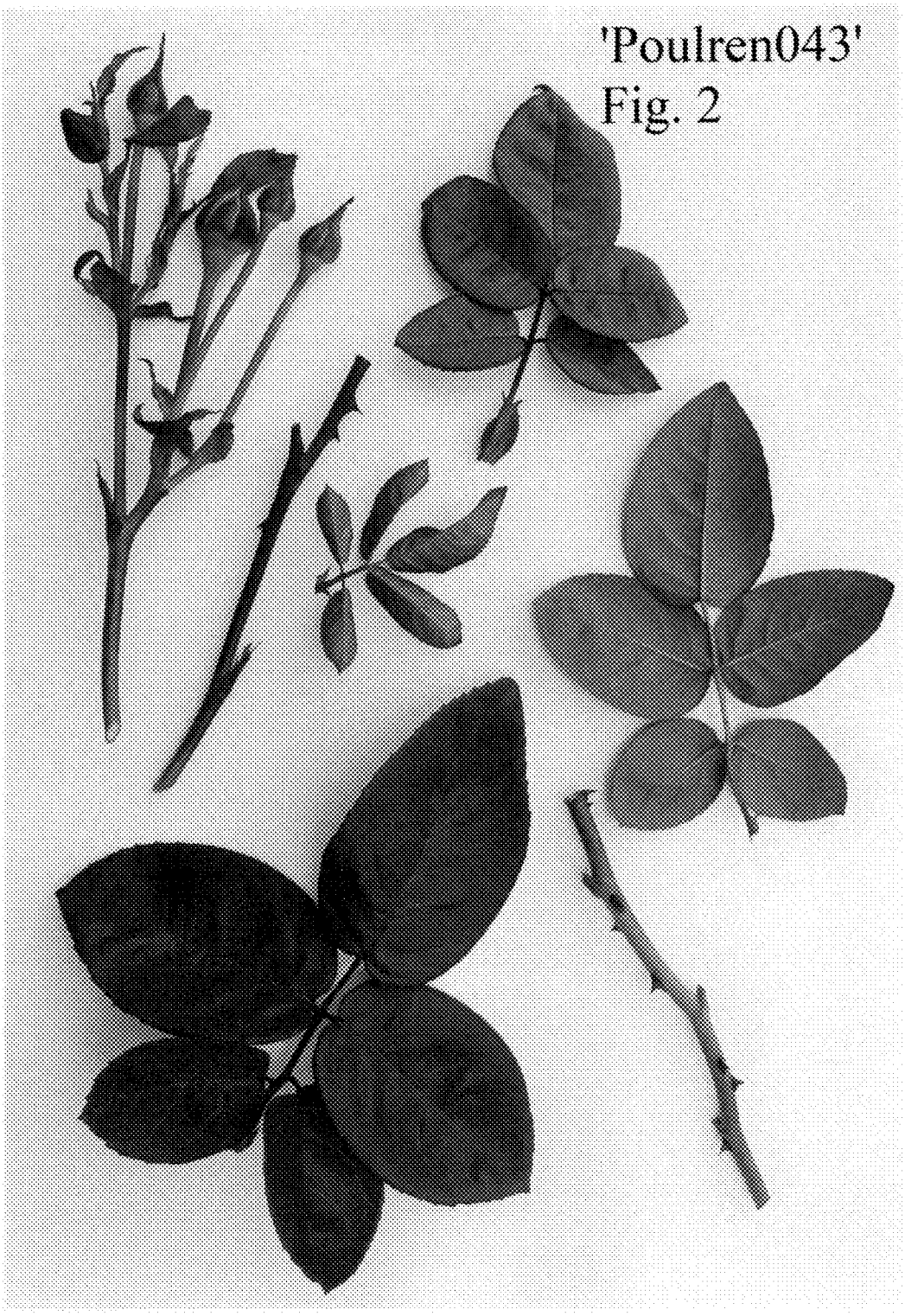

Specifically illustrated in FIG. 2 of the drawings are mature and juvenile leaves, bare mature and juvenile stems exhibiting prickles, and a cluster of flower buds on the branch.

Plants shown are 2 years of age.

DETAILED DESCRIPTION OF THE VARIETY

The following is a description of 'Poulren043 ', as observed in its growth in an outdoor nursery in Odense Denmark. Observed plants are 15 months of age, and were grown on their own roots in 32 cm pots. Color references are made using The Royal Horticultural Society (London, England) Colour Chart, 2001, except where common terms of color are used.

For a comparison, several physical characteristics of the rose variety 'Poulren023', U.S. Plant Pat. No. 27,656 are compared to the claimed plant 'Poulren043'. For the comparison variety open flowers have a general tonality of Red Group 49A and Red-Purple Group 62D. For the claimed plant open flowers have a general tonality of Red Group 56A. While the comparison variety has a flower petal count of 30, the claimed plan has 100 petals.

Flower and Flower Bud

Blooming habit: Continuous.

Flower bud:

- *Size.*—Upon opening, 28 mm in length from base to of receptacle to end of bud. Bud diameter is 18 mm.
- *Bud form.*—Urceolate.
- *Sepal inner surface.*—Color: Yellow-Green Group 146C with intonations of Greyed-Purple Group 185B. Surface: Lightly pubescent.
- *Sepal outer surface.*—Color: Yellow-Green Group 144A with intonations of Greyed-Purple Group 183A. Texture: Smooth.
- *Sepal shape.*—Apex: Cirrhose. Base: Flat at union with receptacle.
- *Sepal Margin.*—Margins have weak foliaceous appendages on three of the five sepals.
- *Sepal size.*—About 23 mm long, 13 mm wide.
- *Receptacle.*—Texture: Smooth. Size: About 10 mm in height, 11 mm wide. Color: Yellow-Green Group 144A. Shape: Campanulate.
- *Pedicel.*—Surface: Smooth. Length: About 50 mm. Diameter: 3 mm on average. Color: Yellow-Green Group 144A with intonations of Greyed-Purple Group 183B. Strength: Strong.
- *Peduncle.*—Length: 3 to 4 cm. Diameter: About 4 mm. Color: Yellow-Green Group 144A with intonations of Greyed-Purple Group 183B. Texture: Smooth.

Flower bud development: Flower buds are borne in clusters of 3 to 5 flower buds per stem.

Flower bloom:

- *Fragrance.*—Very strong perfume.
- *Duration.*—The blooms have a duration on the plant of approximately 14 days. Petals fall cleanly away from plant after flowers have fully matured.
- *Size.*—Flower diameter is 90 mm when open. Flower depth is 36 mm.
- *Flower shape.*—Partially opened cup, very double flower, with petals that curve out from the center.
- *Shape of flower, side view.*—The upper portion is flat. The lower portion is concave.

Petalage: Under normal conditions, flowers have about 100 petals.

General tonality of flower: Open flowers are Red Group 56A.

Petal color:

- *Upon opening, outer petals.*—Upper surface: Red Group 56B and White Group N155B. Lower surface: Red Group 56B and White Group N155B.
- *Upon opening, inner petals.*—Upper surface: Red Group 49C. Yellow Group 11C at basal zone. Lower surface: Red Group 56B and White Group N155B. Yellow 4D at basal zone.
- *Basal petal spots, upon opening.*—Upper surface: Green-White Group 157A, 3 to 4 mm in size. Lower surface: Green-White Group 157A, 3 to 4 mm in size.
- *After opening, outer petals.*—Upper surface: White Group N155B with light intonations of Red Group 56C at marginal zone. Lower surface: White Group N155B with light intonations of Red Group 56C at marginal zone.
- *After opening, inner petals.*—Upper surface: White Group 155C with marginal intonations of Red Group 56B. Lower surface: White Group 155C with marginal intonations of Red Group 56B.

Petals:

- *Petal reflex.*—None.
- *Margin.*—Up to 8 clefts at the margin apex. Moderately undulated.
- *Shape.*—Broad round. Apex shape: Rounded. Base shape: Rounded.
- *Size.*—About 52 mm (l)×50 mm (w).
- *Texture.*—Smooth.
- *Thickness.*—Average.

Petaloids:

- *Size.*—12 mm (l) by 8 mm (w).
- *Quantity.*—About 25.
- *Shape.*—Elliptical with an acute base and rounded apex.
- *Color.*—Red Group 49A and 49B, with Yellow Group 4D at basal zone.

Reproductive flower parts:

- *Pollen.*—None observed.
- *Anthers.*—Size: 3 mm in length. Color: Greyed-Yellow Group 162A and Greyed-Orange Group N163A. Quantity: 35 on average.
- *Filaments.*—Color: Green-White Group 157A. Length: 7 mm.
- *Pistils.*—Length: 4 mm. Quantity: 25 on average.
- *Stigmas.*—Color: Greyed-Yellow Group 160D.
- *Styles.*—Color: Red-Purple Group 58C.
- *Location of stigmas.*—Inferior in location relative to the length of the filaments and the height of the anthers.
- *Hips.*—None Observed.

Plant

Plant growth: Upright. Plants are 40 to 45 cm in height, and 36 cm wide.

Stems:

*Color of juvenile growth.*—Yellow-Green Group 144A/ with strong intonations of Greyed-Purple Group 183A.

*Color of mature growth.*—Yellow-Green Group 144A.

*Length.*—Canes are about 28 cm from the base of the plant to the flowering portion.

*Diameter.*—About 8 mm.

*Internodes.*—On mature canes about 40 mm between nodes.

*Surface texture.*—Young wood: Smooth. Older wood: Smooth.

Long prickles:

*Incidence.*—9 prickles per 10 cm of stem.

*Size.*—Average length of prickles on mature stems is 6 mm.

*Shape.*—Upper portion is linear. Lower portion is concave.

*Color.*—Juvenile prickles: Greyed-Purple Group 187A. Mature prickles: Greyed-Purple Group 183A.

Plant foliage:

*Compound leaf.*—175 mm long×165 wide.

*Quantity.*—2 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 146B.

Plant leaves and leaflets:

*Stipules.*—Size: 12 mm long, 2 mm wide. Quantity: 2 per compound leaf. Shape: Linear, slightly broad based with outward extending apices. Margins: Finely serrated. Color: Yellow-Green Group 146A.

*Petiole.*—Length: 30 mm. Diameter: 2 mm. Upper surface color: Yellow-Green Group 144A. Lower surface color: Yellow-Green Group 144A.

*Rachis.*—Length: 41 mm. Upper surface color: Yellow-Green Group 144A with strong intonations of Greyed-Purple Group 187A. Lower surface color: Yellow-Green Group 144A.

*Leaflet.*—Quantity: Normally 5 leaflets. Margins: Serrated. Size: Terminal leaflets are about 72 mm long, 50 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phraginidium* spp., black spot *Diplocaipon rosae*, and *Botiytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren043' substantially as described and illustrated herein.

* * * * *

'Poulren043'

'Poulren043'